US00PP21542P3

(12) United States Plant Patent
Zwetzig et al.

(10) Patent No.: US PP21,542 P3
(45) Date of Patent: Nov. 30, 2010

(54) ***HIBISCUS* PLANT NAMED 'STRAWBERRY SWIRL'**

(50) Latin Name: *Hisbiscus*
Varietal Denomination: Strawberry Swirl

(76) Inventors: Gretchen Angela Zwetzig, 267 N. Strathmore Ave., Lindsay, CA (US) 93247; David Whitman Fleming, Lincoln, NE (US); Gretchen Zwetzig, legal representative, 267 N. Strathmore Ave., Lindsay, CA (US) 93247

( * ) Notice: Subject to any disclaimer, the term of this patent is extended or adjusted under 35 U.S.C. 154(b) by 0 days.

(21) Appl. No.: 12/317,182

(22) Filed: Dec. 18, 2008

(65) Prior Publication Data

US 2010/0162449 P1 Jun. 24, 2010

(51) Int. Cl.
*A01H 5/00* (2006.01)

(52) U.S. Cl. ..... Plt./257

(58) Field of Classification Search ..... Plt./257
See application file for complete search history.

*Primary Examiner*—Susan B McCormick Ewoldt

(57) ABSTRACT

A new and distinct cultivar of winter hardy *hibiscus* plant named "Strawberry Swirl" is the result of a unique hybridization. This new and distinct cultivar is characterized primarily to its novelty by, its extreme cold hardiness to Zone 4, large, pinwheel-shaped, pink and white flowers and its "maple-shaped" green foliage, compactness of about 3 feet, its vigorous and uniform breaking habit and its floriferous nature from midsummer until frost.

2 Drawing Sheets

BACKGROUND OF THE NEW PLANT

The new plant of this invention is the result of a unique hybridization, with the breeding achievement being evidenced in the outstanding combination of characteristics exhibited by this new and distinct *Hibiscus* plant, which include:

(a) Refined, 3-5 lobed "maple-shaped" leaves of a green color and relatively smooth margins which combined compliments the landscape;

(b) Medium to large-sized flowers that are outstanding for their bold dark and light pink and white colored, pin wheel-like under turned petals;

(c) The plant being very floriferous with flowers that stay open for at least one to two days;

(d) The plant being medium-sized but vigorous with compact and uniform breaking action which gives it unique landscape utility; and (e) The plant being so hardy that it can consistently withstand winter temperatures of at least −30 degrees Fahrenheit.

SUMMARY OF THE INVENTION

'Strawberry Swirl' was the result of a 40-year breeding program. Its ancestry includes *Hibiscus moscheutos* and *Hibiscus coccineus*. More specifically, the plant resulted from multiple crossings with an unnamed, Fleming-bred *Hibiscus moscheutos* (non patented) and an unnamed Fleming-bred *Hibiscus coccineus* (non patented). The seedling which most nearly met all of the above standards was selected.

This new plant first bloomed in the summer of 1998 and was selected by David Fleming and Gretchen Zwetzig on David Fleming's property located at 8101 S. 14th St. 68512 Lincoln, Nebr. (previous address for applicants). Asexual propagation of the plant in Lincoln, Nebr. by cuttings and root division has shown that the unique and distinguishing features of the plant are faithfully transmitted from generation to generation and appear to be fixed.

Since its origin, the plant has bloomed from midsummer until frost, while exhibiting the aforementioned distinctive characteristics. This hardy *Hibiscus* plant greatly contributes to the market with its, sheer beauty and utter refinement, its compact growth habit, its enhanced resistance to disease and insects, its stability through extremes in rain and drought, and its extreme hardiness.

BRIEF DESCRIPTION OF THE DRAWINGS

The flower and foliage of the cultivar at two years of age are shown in the attached drawings. More specifically.

Figure 1:
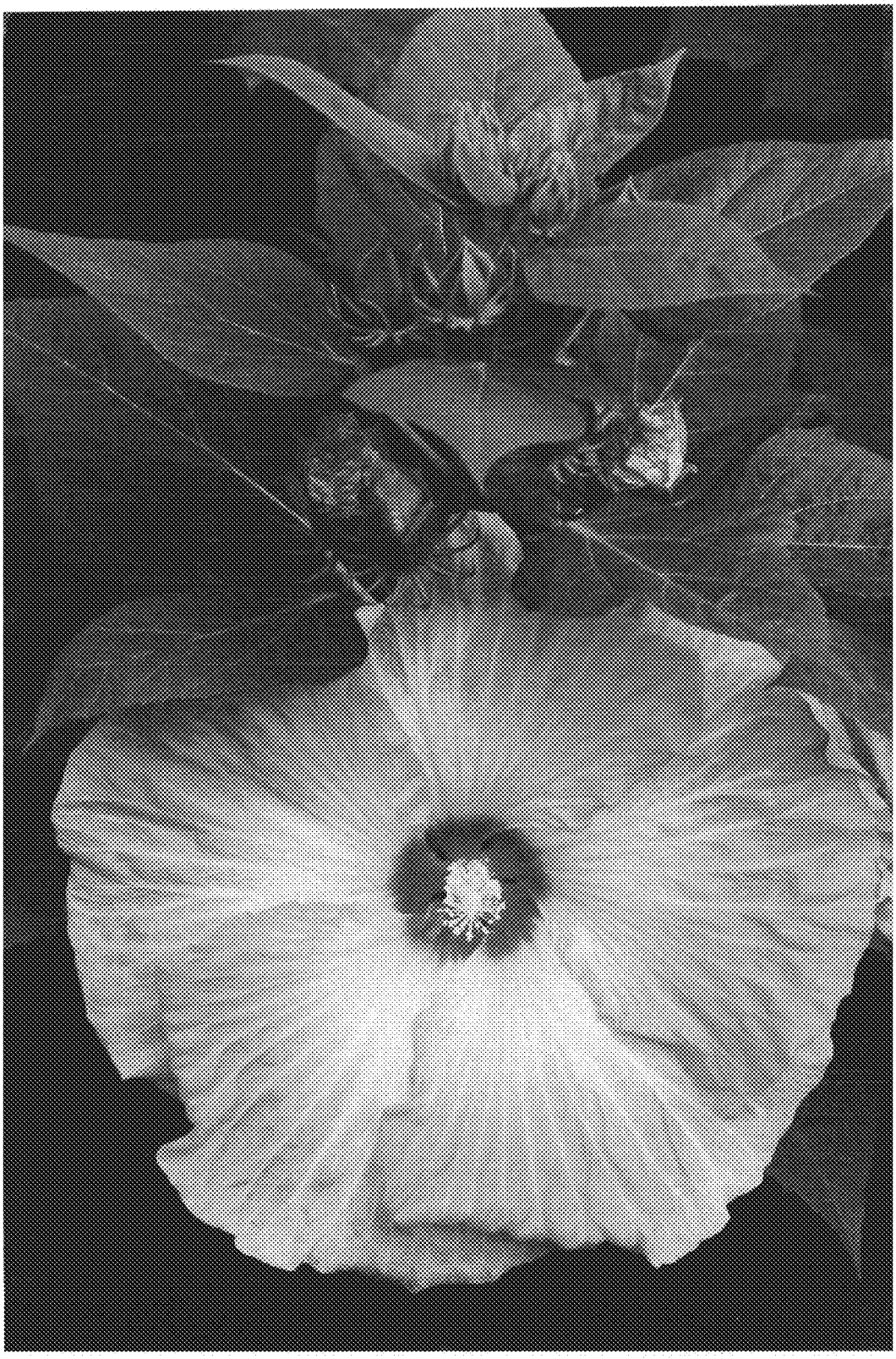
FIG. 1 is a close-up of the flower and the leaf.
Figure 2:
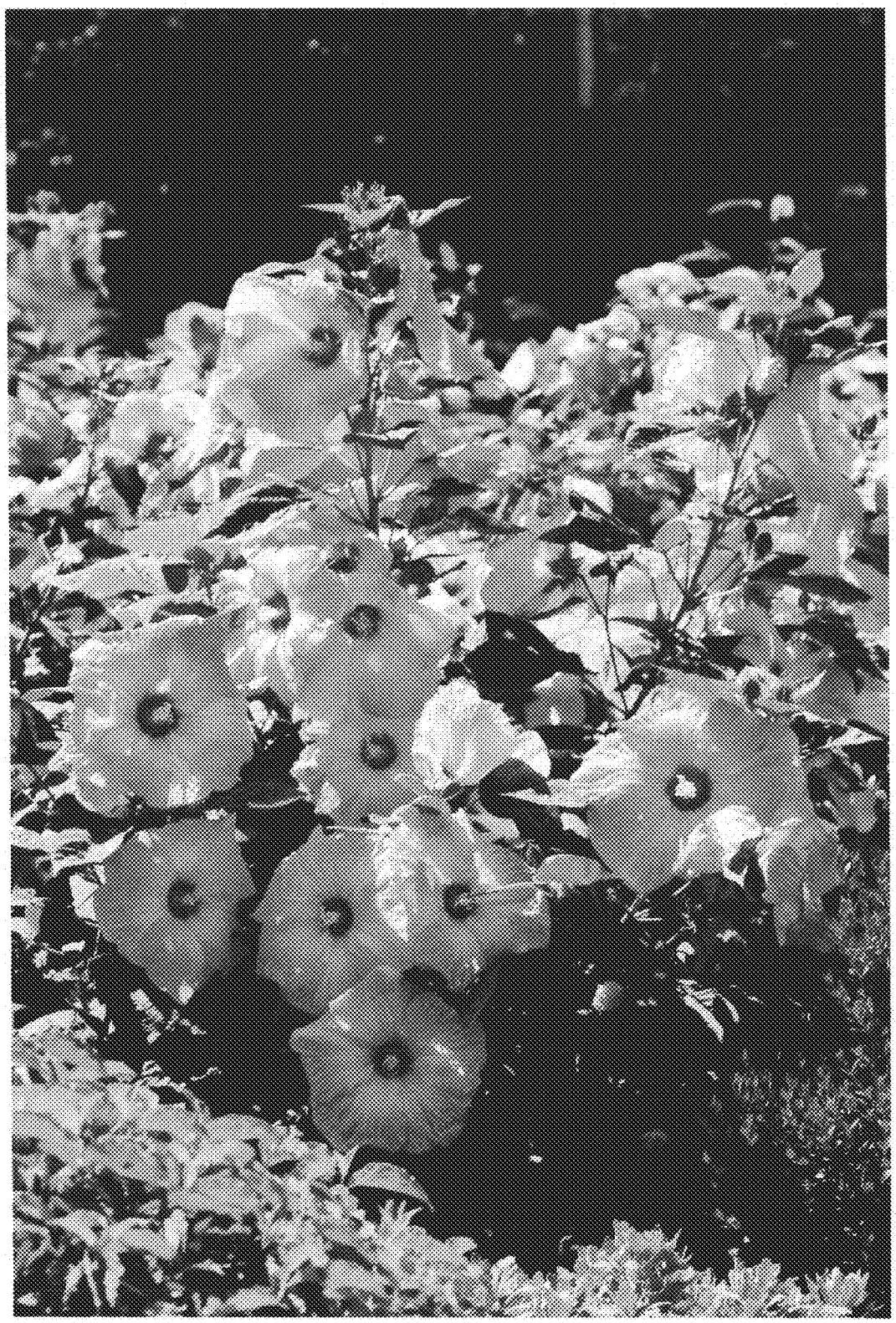
FIG. 2 is of the whole plant.

The colors are as true as is reasonably possible to attain in photographic illustrations of this type. The colors illustrated may be slightly off due to light reflectance.

DESCRIPTION OF THE NEW PLANT

What follows is a detailed description of the new cultivar. The specific color descriptions are in accordance with The Royal Horticultural Society Colour Chart, while general color recitations are consistent with ordinary American terminology.

'Strawberry Swirl' has not been observed under all possible environmental conditions. It is to be understood that the phenotype may vary significantly with variations in the environment such as temperature, light intensity, humidity, and day length without, however any difference in genotype of the plant. The following botanical characteristics and observations are gathered from the plant when grown in Lincoln, Nebr. (USDA Zone 4).

THE PLANT

Parentage:

*Seed Parent.—Hibiscus moscheutos,* unnamed and unpatented Fleming-bred seedling.

*Pollen Parent.—Hibiscus coccineus,* unnamed and unpatented Fleming-bred seedling.

Comparison between parents and observed plant: Parent plants differ being 1 foot taller. Parent plants flowers are also approximately 1 inch smaller.

Comparison between observed plant and other known cultivars: Though Observed plant is unique, it improves the pinwheel-type flower of 'Turn of the Century'. But, Observed Plant is much shorter with much bigger and more colorful flowers and more hardiness. Observed Plant is most similar to Co-Pending application Ser. Nos. 12/317,167, 12/317,181, 12/317,183 and the other patented hardy *Hibiscus* by Flemings Flower Fields, in that: (a) They are all more compact at 3 foot in height on average. (b) They are all hardy to −30 degrees Fahrenheit. (c) They all have refined, new leaf shapes. (d) They all have thick, new flowers with new colors that bloom from the top to the bottom of the plant.

Origin: A selected seedling from stated cross.

Type of plant: Hardy, herbaceous perennial.

Classification: Variety of hardy *Hibiscus* plant.

Propagation: Relatively easy to propagate by cuttings in approximately 2 weeks; holds its distinguishing characteristics through successive cuttings and divisions.

Size: About 3 feet (97 cm) tall and about 2½ feet wide.

Form: Symmetrical annual growth from perennial roots.

Habit: Upright and uniformly branched.

Growth: Vigorous; medium and compact. Full grown (3-3½ ft) in 2 years.

Hardiness: Hardy to at least −30 degrees Fahrenheit.

General health: Plant is very disease resistant against rot, aphids, spider mites, scale, white fly etc.; sturdy through excessive drought, rain or wind.

*Foliage.*—1. Arrangement: Alternate. 2. Shape: Juvenile: 3-5 lobed "Ovate to maple-shaped" leaves. Rounded base shape. Mature: Refined, "Ovate to maple-shaped", 3-5 lobed leaf with entire to mildly serrate margins and acute apices; rounded base. 3. Size: Mature leaf (petiole base to apex): Length is about 5¾ inches or 14½ cm, width is about 5 inches or 13 cm. 4. Color: Young leaves (upper side): 146 and 147-A. Mature leaves: (upper side): 146 and 147-A. Veins: 144-C. Venation pattern: Palmate. Venation color: 146-A. Coloration of the lower leaf surface: 147-B. 5. Surface texture: Upper: Smooth. Lower: Semi-smooth. 6. Petiole length: About 2¾ inches or 6.5 cm. Petiole diameter: 1-2 cm. 7. Petiole color: 147-B.

Stems: The stems are stout at the base, becoming more slender toward the apices; coloration is consistent with the petiole.

*Stem length.*—2-3 inches.

*Stem diameter.*—2 cm. Internode length: 2 inches.

*Stem texture.*—Smooth.

Stem color: 148B.

THE FLOWER

Blooming period: Profuse from July until frost.

Flower diameter: Large; about 10-12 inches (27 cm).

Borne: Singly in leaf axils, from midpoint of stems upward.

Bloom duration: Individual bloom lasts at least one to two full days.

Form: Campanulate; petals are also very overlapping.

Average number of flowers per season: 300.

*Bud.*—1. Length: About 3½ inches or (8.8 cm) on day before opening. Diameter: 1½-2 inches. 2. Color: 60-A. 3. Surface texture: Semi-glabrous. 4. Duration: One to two weeks.

*Corolla.*—Having five petals. 1. Petal character and dimensions: Campanulate and very overlapping. (a) Length: About 4½ inches or (11.5 cm). (b) Width : About 5¾ inches or (14.5 cm). 2. Coloration: Bright reddish-pink, medium pink, light pink, and white. (a) Midpoint to margins of petal: Between 68-A and N 66-C; also 76-C and 76-D. Coloration of lower petal surface: 69-C. (b) Venation in petals: 61-A. (c) Eye zone: Between 59-A and N 77-A. Size: 1¾ inches or (5 cm). 3. Texture: Smooth. 4. Substance: Thick. 5. Shape: Campanulate and very overlapping with petal folds at edges.

Reproductive organs:

1. *Staminal column.*—Stamen along basal two-thirds. Stamen length: About 1¼ inches or (3.5 cm). Stamen color: 155-A. Pollen color: Lighter than 5-D.
2. *Style.*—Terminates upper one-third of staminal column. Stigmatic lobe color: Somewhere between 60-A and 60-B.

Calyx: Connate at the base; about 1¼ inches or (3.5 cm) in length.

*Color.*—Medium green. 147-B.

Stipules: None.

*Epicalyx.*—Whorl of bracts. 1. Shape: 10-12 slender, sword-shaped bractlets. 2. Length: About 1½ inches or (3.8 cm). 3. Color: 144-A and 144-B.

*Penduncle.*—1. Length: About 3 inches or (7.6 cm). 2. Strength: Stiff and sturdy. 3. Color: Light to medium green between 144-A and 144-B.

Seeds:

*Size.*—1 cm.

*Color.*—Grey.

*Average number.*—Less than 100 per plant.

GENERAL OBSERVATIONS

This plant, as a hybridized hardy *Hibiscus,* is valuable to the landscape market for its improvements in thicker textured and brightly colored flowers and buds, refined "maple-like" green foliage, its all-around vigor, good breaking action, and adaptation to extreme environments, including the ability to consistently survive winter temperatures of at least −30 degrees Fahrenheit.

The claim:

1. A new and distinct cultivar of hardy *Hibiscus* plant, as herein shown and described, characterized by its compact nature, refined "maple-shaped" foliage of a green coloration, its large bold, pink and white "pinwheel-like" flowers, its vigor and its hardiness.

* * * * *